United States Patent [19]

Kritzman et al.

[11] Patent Number: 5,045,282
[45] Date of Patent: Sep. 3, 1991

[54] OPTICAL FIBER SENSING DEVICE FOR ANALYSIS

[75] Inventors: Amnon Kritzman; Eliezer Falkenstein, both of Zichron Yaakov; Moshe Ish-Shalom; Alla Buch, both of Haifa; Menuha Beer, Haifa, all of Israel

[73] Assignees: Optical Chemical Tech. Ltd., Zichron Yaakov; Israel Ceramic & Silicate Inst., Haifa, both of Israel

[21] Appl. No.: 257,929

[22] Filed: Oct. 14, 1988

[30] Foreign Application Priority Data

| Oct. 16, 1987 | [IL] | Israel | 84181 |
| Oct. 16, 1987 | [IL] | Israel | 84182 |
| Nov. 19, 1987 | [IL] | Israel | 84531 |
| Nov. 19, 1987 | [IL] | Israel | 84533 |

[51] Int. Cl.⁵ .................. G01N 21/64; G01N 21/77
[52] U.S. Cl. .................. 422/56; 128/634; 250/227.14; 250/483.1; 422/57; 422/58; 422/82.06; 422/82.07; 422/82.08; 422/82.11; 436/164; 436/169; 436/172
[58] Field of Search .................. 422/55-58, 422/61, 82.06, 82.07, 82.08, 82.11; 250/227.14, 459.1, 461.1, 461.2, 483.1; 128/634; 350/96.34; 436/164, 172, 169

[56] References Cited

U.S. PATENT DOCUMENTS

| Re. 31,832 | 2/1985 | Samulski | 250/459.1 X |
| Re. 31,879 | 7/1985 | Lubbers et al. . | |
| 4,003,707 | 1/1977 | Lubbers et al. | 128/634 X |
| 4,123,227 | 10/1978 | Heim et al. . | |
| 4,194,877 | 3/1980 | Peterson . | |
| 4,200,110 | 4/1980 | Peterson et al. . | |
| 4,201,222 | 5/1980 | Haase . | |
| 4,272,484 | 6/1981 | Lubbers . | |
| 4,306,877 | 12/1981 | Lubbers . | |
| 4,344,438 | 8/1982 | Schultz . | |
| 4,476,870 | 10/1984 | Peterson et al. . | |
| 4,509,370 | 4/1985 | Hirschfeld . | |
| 4,544,231 | 10/1985 | Peterson . | |
| 4,557,900 | 12/1985 | Heitzmann . | |
| 4,568,518 | 2/1986 | Wolfbeis et al. . | |
| 4,580,059 | 4/1986 | Wolfbeis et al. . | |
| 4,587,101 | 5/1986 | Marsoner et al. . | |
| 4,597,392 | 6/1986 | Opitz et al. . | |
| 4,599,901 | 7/1986 | Hirschfeld . | |
| 4,632,807 | 12/1986 | Marsoner . | |
| 4,640,820 | 2/1987 | Cooper . | |
| 4,657,736 | 4/1987 | Marsoner et al. . | |
| 4,706,677 | 11/1987 | Goorsky et al. | 128/634 |
| 4,919,891 | 4/1990 | Yafuso et al. | 422/82.08 X |

FOREIGN PATENT DOCUMENTS

| 0072627 | 2/1983 | European Pat. Off. . |
| 0074055 | 3/1983 | European Pat. Off. . |
| 0105870 | 4/1984 | European Pat. Off. . |
| 0135746 | 4/1985 | European Pat. Off. . |
| 0205232 | 12/1986 | European Pat. Off. . |
| 0214768 | 3/1987 | European Pat. Off. . |
| 1190583 | 5/1970 | United Kingdom . |

OTHER PUBLICATIONS

Offenbacher et al., Fluorescence Optical Sensors for Continuous Determination of Near-Neutral pH Values, Sensors and Actuators, 9 (1986), 73-84.
Gehrich et al., Optical Fluorescence and its Application to an Intravascular Blood Gas Monitoring System, IEE Trans. Biomed. Engin., 2 (1986), 117-132.
Seitz, W. R., Chemical Sensors Based on Fiber Optics, Analytical Chem. 56 (1984), 16A-34A.

Primary Examiner—Robert J. Hill, Jr.
Attorney, Agent, or Firm—Joseph Scafetta, Jr.

[57] ABSTRACT

A sensing device for use in the manufacture of an optic probe apparatus for quantitative determination of the chemical properties of a medium in situ includes at least one glass optical fiber.

19 Claims, 2 Drawing Sheets

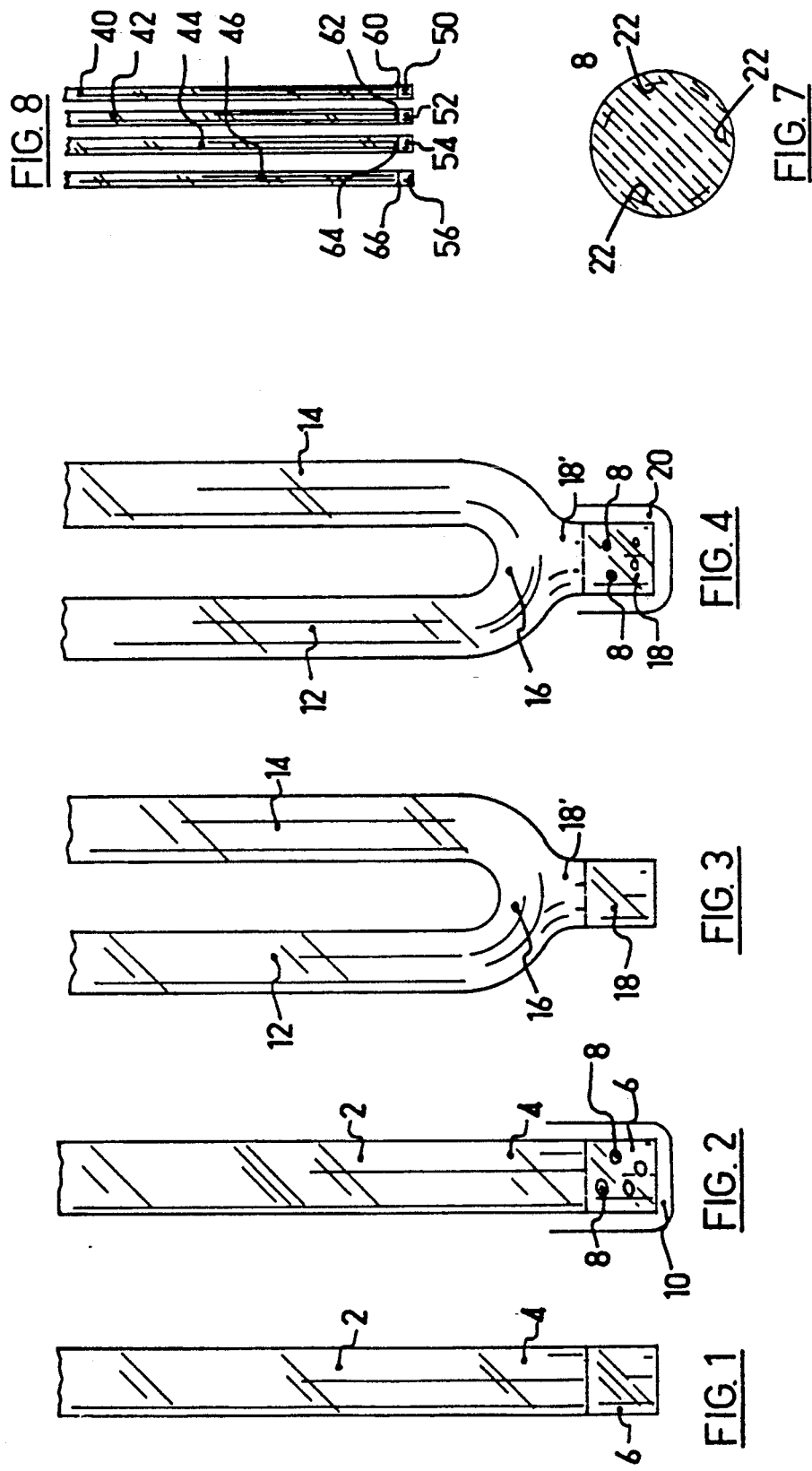

OPTICAL FIBER SENSING DEVICE FOR ANALYSIS

FIELD OF THE INVENTION

The present invention relates to a sensing device for use in the manufacture of an optic probe apparatus for quantitative determination of the chemical properties of a medium in situ, to a process for making such device, to said apparatus incorporating such device and to optical fibers for use therein.

BACKGROUND OF THE INVENTION

Optic probes for quantitative determination of certain chemical properties of the blood in situ, are known. Thus, in U.S. Pat. No. 4,476,870 (Peterson), which issued Oct. 16, 1984, and the contents of which are incorporated by reference herein, there is described such a probe intended for determining the partial pressure of oxygen in the blood or tissue of a living animal. This probe comprises one or two strands of plastic optical fibers terminating in an elongate section of porous polymer tubing which is packed with a fluorescent visible light-excitable dye placed on a porous adsorptive particulate polymeric support. While many compounds which are excited by ultraviolet light are known, and the intensity of the emitted light of such compounds may be sensitive to the presence of oxygen, Peterson used plastic optical fibers, because (inter alia) he regarded the use of inorganic fibers as impractical for the desired purpose because of brittleness. Also, since plastic optical fibers are insufficiently transparent to ultraviolet light, this necessitated the use by him of visible light and of dyes sensitive thereto.

As will be seen from the description herein, and contrary to the teaching of Peterson, the present inventors have found the use of certain inorganic optical fibers to be eminently practical for the purposes of the present invention, and brittleness is not a problem. Moreover, the use of a sensitized porous glass tip at the end of a glass optical fiber, enables the manufacture of optical probe apparatus which is believed to be considerably more sensitive than that of Peterson. Furthermore, the use according to the present invention of such a tip has the result that the sensor can be much smaller than, and is therefore potentially of greater flexibility and applicability than Peterson's probe. Unpublished experiments by the present inventors have shown that in fact no more than an ambit of about 200 microns of Peterson's probe is the realistic sensitive volume.

In U.S. Pat. No. 4,568,518 (Wolfbeis), which issued Feb. 4, 1986 (the contents of which are incorporated by reference herein), there is described a flexible sensor element comprising a carrier membrane and an immobilized network structure (especially one based on cellulose) including a fluorescent indicator, and in particular such an indicator for measurement of pH values and for blood gas analysis. Wolfbeis's object appears to be to load the carrier with as much indicator as possible and he takes the view that "all known methods of immobilization pertaining to glass surfaces suffer from the disadvantage that the surface will take up only a relatively small amount of bonded immobilized material in a single layer".

Contrary to the teaching of Wolfbeis, however, the present inventors have found that the fact that glass surfaces may only immobilize a relatively small amount of material (in the present invention the relevant material is adsorbed on internal surfaces of the glass, optimally in a single layer) is to be regarded as an advantage and not a disadvantage. This is because when much more than a molecular layer of fluorescent material is immobilized on a carrier, the fluorescent molecules under excitation may tend to react physically with each other, the effect of which will be to substantially reduce the number of excited molecules which give the desired information.

In European Patent Application No. 0214768 (Hirschfeld), published Mar. 18, 1987, the contents of which are incorporated herein by reference, physical and chemical properties of a sample fluid are monitored by measuring an optical signal generated by a fluorescent substance and modulated by an absorber substance. In practice, both fluorescent and absorber substances may be adsorbed on or/and covalently bonded to glass in the form of porous or sintered glass, or a colored filter glass may be used alternatively as substrate, the substrate in each case being attached by adhesive to one end of a fiber optic. There is no suggestion in this European Patent Application either that the fluorescent substance may be used in absence of the absorber substance, or that the device of the invention may be used for the measurement of chemical properties of the blood in situ, although the same inventor in U.S. Pat. No. 4,599,901, which issued July 15, 1986 (and the contents of which are incorporated by reference herein) described a method for direct measurement of arterial blood pressure measuring the intensity of emissions from (inter alia) the surface of a plastic bubble coated with a fluorescent composition and attached to the end of a fiber optic. Moreover, the teaching of the use of porous glass in EP 0214768 is restricted to the use of commercially available material which is attached by adhesive to the fiber optic; any concept of attachment in any other manner, or of formation of the porous glass sensor element in situ is completely absent.

In principle, the present invention provides an optical probe device, of which the essential elements are (except for an optional surface polymeric film) virtually completely fabricated from glass without the aid of adhesive, and which it is believed, when having adsorbed on the internal surface thereof one or more light-sensitive substances, are more sensitive than comparable prior art sensors. The sensor element is also much smaller than hitherto, and this enables the device to be used in situations, especially in relation to monitoring the chemical properties of the human blood stream in vivo, which it is believed were not from a practical standpoint possible before the advent of the present invention.

It will be seen infra that the present invention makes use of substantially non-porous glasses ("parent glasses") which are convertible to porous glasses. Both parent glasses and porous glasses are well known in the art. When parent glasses, which may be certain borosilicate glasses, are heat-treated there results an interconnected separation of phases, one of which may be leached by acid (or in certain cases even by water) to leave an insoluble mainly silica phase (in fact, a porous glass) which could be consolidated by heating into a dense, clear glass known in the trade as "Vycor". Since it is the porous glass which is the desirable carrier for light-sensitive substance in accordance with the present invention, any such consolidation step as is used to produce "Vycor" glass is of course omitted herein.

Composition ranges for parent glasses, which are to be regarded as illustrative only, are:
(1) $SiO_2$ 55–70, $Na_2O$ 10–0.1, $B_2O_3$ balance to make 100%;
(2) $SiO_2$ 55–70, $K_2O$ 9–0.1, $B_2O_3$ balance to make 100%;
(3) $Al_2O_3$ 0.1–4, $SiO_2$ [55 minus 1.25 × $Al_2O_3$ content] up to 70, $Na_2O$ 10–0.1[minus 0.17 × $Al_2O_3$ content], $B_2O_3$ balance to make 100%;
(4) $SiO_2$ 55–75, alkalis 5–15, oxides of Fe, Co, Ni 5–15, $B_2O_3$ 15–30%.

Literature references to porous glasses are also included in the above-cited European Patent Application.

In GB 1190583 (Bergman), published May 6, 1970, there is described a gas detector for measuring or monitoring the partial pressure of a gas (in particular, oxygen), containing a matrix support for luminescent material. The matrix, which in practice is used in the form of a thin film or disc, may be made of "porous Vycor-type glass". No details are provided of how such glass is obtained. In his illustrated embodiment, a sintered metal cylinder contains the matrix, an ultraviolet glow lamp, filters and photoelectric cells. The atmosphere to be monitored either diffuses through the wall of the cylinder, or is led through the apparatus by inlet and outlet pipes. This patent is not concerned with the use of fiber optics, with a detector element of such a size that it may constitute or be attached to the tip of a fiber optic, or with monitoring the chemical properties of the human blood stream in vivo.

SUMMARY OF THE INVENTION

The invention thus provides in one aspect a sensing device for use in the manufacture of an optic probe apparatus for quantitative determination of the chemical properties of a medium in situ. In one embodiment, this device comprises essentially at least one glass optical fiber means, to each of which is attached by fusion at an open end thereof a discrete glass tip, the glass of said tip being selected from substantially non-porous glasses convertible to porous glasses. Following fusion, the discrete glass tip may be converted to a porous glass tip, and the latter may be treated so as to adsorb on the internal surface thereof at least one substance selected from fluorescent and other light sensitive substances. In another embodiment, the sensing device comprises essentially at least one glass optical fiber means fabricated from a substantially non-porous glass convertible to a porous glass, each of which at an open end thereof has been treated to convert the tip thereof to a porous glass tip integral with said optical fiber means. The present invention also relates to glass optical fiber means for use in the manufacture of optic probe apparatus characterized by the fact that it is fabricated from a substantially non-porous glass convertible to a porous glass. The sensing device of the invention may be made, e.g., by a process comprising the step of attaching by fusion a glass tip to an open end of each one of at least one glass optical fiber means, and wherein the glass of said tip is selected from substantially non-porous glasses convertible to porous glasses, or alternatively by a process comprising the step of treating an open end at the tip thereof of each one of at least one glass optical fiber means fabricated from a substantially non-porous glass convertible to a porous glass, thereby to convert the or each tip to a porous glass tip.

According to yet a further aspect of the invention, there is provided an apparatus for quantitative determination of the chemical properties of a medium in situ, characterized by the fact that it comprises as an optic probe a sensing device as described above, in which the or each porous glass tip has been treated so as to adsorb on the internal surface thereof at least one substance selected from fluorescent and other light sensitive substances. Notwithstanding the use of the term "adsorb" in connection with the description of the attachment of the fluorescent or other light sensitive substances to the internal surfaces of the or each porous glass tip, it is to be understood that the present invention is not to be limited to any particular manner of attachment of these substances. From a practical point of view, these substances must be securely held to the internal surfaces when the sensing apparatus is in use; thus, it is contemplated that the fluorescent or other light sensitive substances may be either physically or chemically attached to the internal surfaces, so long as the attachment is secure.

BRIEF DESCRIPTION OF THE DRAWINGS

FIG. 1 shows in section a sensing device according to an embodiment of the invention which comprises a single unbranched glass optical fiber.

FIG. 2 shows in section a sensing device according to a further embodiment of the invention which comprises a single unbranched glass optical fiber.

FIG. 3 shows in section an example of a sensing device according to the invention which comprises two glass optical fibers which in one embodiment are attached to a single glass tip and in another embodiment are fused together at one end.

FIG. 4 shows in section another sensing device according to the invention which comprises two glass optical fibers which in one embodiment are attached to a single glass tip and in another embodiment are fused together at one end.

FIG. 7 shows in section adsorption of active material on the inner surface of a single pore of a porous glass tip.

FIG. 8 shows in section a bundle of optical fibers attached to respective glass tips.

DETAILED DESCRIPTION OF THE INVENTION

Figure 6:
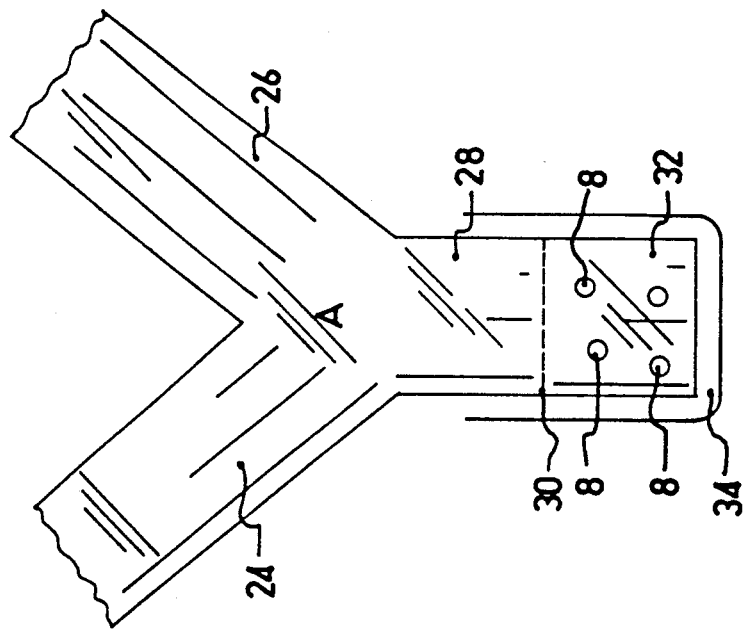
FIG. 6 shows in section a sensing device according to a further embodiment of the invention which comprises a Y-shaped glass optical fiber.

It is to be understood that the device of the invention comprises in one embodiment a glass tip either fused to or integral with an open end of glass optical fiber means (or a plurality of glass tips fused to or integral with respective open ends of a plurality of glass optical fiber means), which when used as the sensor of an optic probe will have been made porous, and will then have adsorbed on the internal surface thereof at least one light sensitive substance.

It is believed that the glass optical fibers utilized to make the sensors of the present invention according to the embodiment in which the or each porous glass tip is integral with the optical fibers constitute in themselves a novel and inventive article of manufacture. This embodiment of the invention, which enables for the first time a sensor integral with a glass optical fiber to be manufactured, represents for this very reason a major step forward in the art of optic sensors.

A "light sensitive substance" in the present context means a substance which will react to incident light by emitting a light signal. It is presently preferred that this substance is an agent which imparts information exclusively by means of the internally unmodified intensity of the light emitted therefrom. In other words, it is preferred not to add any substance, such as the absorber of EP 0214768, which will vary the intensity of the emitted light signal. The intensity of the emitted signal will of course be modified by an external agent, namely, by the particular chemical property of the medium, the determination of which is desired.

The sensitivity of such substance (which may be a fluorescent substance) to light, e.g. visible or ultraviolet light, will be affected by the chemical properties of the medium in which the sensor is inserted. While it is presently contemplated that the device of the present invention will be applicable to the quantitative determination of the chemical properties of any medium, as e.g. a reaction medium of a chemical industrial process, nevertheless it is believed that it will be especially useful in respect of such determinations made on blood or blood cells, and more particularly for the determination in vivo of chemical properties of blood, such as pH and the partial pressure of oxygen and of carbon dioxide. In other words, the intensity of the light emitted from the substance or substances adsorbed on the internal surface of the sensor, will be a function of such chemical properties.

In its broadest aspect, however, the device of the invention is not confined to the instance where the glass tip is porous and is sensitized, but also includes the case in which a fused glass tip is non-porous but is convertible to a porous tip, as well as the case in which a fused or integral porous glass tip is porous but is not yet sensitized by having adsorbed on its internal surface one or more light-sensitive substances.

By the expression "at least one glass optical fiber means" it is intended to convey that the invention includes, on the one hand, either one or a plurality of glass optical fiber means, and on the other hand that what is termed "glass optical fiber means" may assume a number of configurations of glass optical fibers. Thus, for example, each glass optical fiber means may be constituted in one or other of the following modes (a), (b) and (c), namely, where: (a) the glass optical fiber means comprises one unbranched glass optical fiber; (b) the glass optical fiber means comprises at least two glass optical fibers all of which are attached to, or are fused together to form, a single glass tip; (c) the glass optical fiber means is Y-shaped, and the glass tip (which is porous or is to be made porous) is located at an open end of one of the arms of the Y. In mode (a), it is evident that both the light directed to the sensor and that emitted therefrom will be channelled along the same optical fiber. In mode (b), it is intended that the light directed to the sensor will be channelled along one (or more) optical fibers, and the emitted light will be mainly channelled along another one (or more) optical fibers. In mode (c), it is intended that the light directed to the sensor will be channelled along one arm of the Y to the junction and thereafter to the sensor (i.e. the sensitized tip), while the emitted light will be channelled from the sensor to the junction and thereafter (mainly) along the other arm of the Y. Whatever the manner in which the or each glass optical fiber means is constituted, the device of the invention may comprise one or a plurality of such glass optical fiber means.

When the device of the invention comprises a single glass optical fiber means, it will be most readily adapted to the determination of a single chemical property. Nevertheless, it is within the scope of the present invention to treat a single porous tip with more than one light sensitive substance which thereby become adsorbed on the internal surface of the porous tip and to measure the light emitted from each such substance present in the porous tip, in order to determine more than one chemical property. In an alternative embodiment of the device of the invention, in which the "at least one glass optical fiber means" comprises in fact a plurality of glass optical fiber means, each of which has attached thereto or integral therewith a different porous glass tip, then that at least two of the tips may have adsorbed thereon different light sensitive substances, respectively, thereby facilitating the determination of at least two different chemical properties of the medium.

For the device according to the invention to be usable in an optic probe, it will be necessary for the (at least one) attached or integral tip to be subjected to a process step whereby the substantially non-porous glass of the tip is converted to a porous glass. This step will normally comprise acid treatment, using e.g. hydrochloric acid, the acid treatment being preceded by a heat treatment. The porous tip or tips thus produced may then be treated so as to adsorb on the internal surface thereof at least one light-sensitive composition, e.g. a fluorescent composition.

It is advantageous, for a number of reasons, for the thus-treated porous discrete glass tip to be coated with a porous polymeric film prior to actual use. Such a film would protect the external glass surface thereof from nicks and scratches, and especially if extended somewhat over the adjacent part of the glass fiber means which is either integral with it or to which it is attached, would also have a safety function in preventing any light sensitive substance, from contaminating the medium under test. (However, tests have shown that it is extremely unlikely that under conditions of use generally prevailing, any light sensitive substance will become detached from the internal surface of glass on which it has been adsorbed.) It will be appreciated that in any event the porosity of the polymeric film will necessarily be such as to allow the ingress of the medium or at least the components thereof which are the subject of quantitative determination. A suitable material for the film would appear to be an RTV silicone such as that marketed under the trade name "Dow Silastic Corning 890 (or 891)", which incidentally has been approved by the FDA for body implants.

As has already been indicated, the invention provides in a further aspect a process for making a sensing device in accordance with the details already described above. In yet another aspect, the invention provides an apparatus for quantitative determination of the chemical properties of a medium in situ, characterized by the fact that it comprises as an optic probe a sensing device in accordance with the details already described above.

The concept of the present invention resides principally in the device comprising glass fiber optic means having integral therewith or fused thereto a glass tip convertible to a porous glass tip, for practical application as a sensor rendering this tip porous, and thereafter treating it with at least one light-sensitive material, so as to adsorb the latter on the internal surface of the porous glass tip. It will therefore be appreciated that in the apparatus aspect of the invention, such features as the means for sending the light to the sensor, receiving light emitted therefrom, and calculating the desired properties from the intensity of the emitted light, will in principle be known, and per se form no part of the present inventive concept.

Examples of suitable materials which fluoresce when subjected to ultraviolet light and which may be useful as the light-sensitive substances for being adsorbed on the internal surfaces of the porous glass tips of the sensing device of the invention, when used for in vivo or in vitro determinations in the blood (or in industrial applications) are as follows:

$O_2$—pyrene and other polycyclic aromatic compounds;

pH and $CO_2$—coumarin derivatives, such as 7-hydroxycoumarin.

Materials fluorescing in light other than UV are also operable.

DETAILED DESCRIPTION OF THE DRAWINGS

It will be appreciated that the drawings are generally schematic and while enlarged compared with the actual size, are not drawn to scale. The same numerals in different drawings depict corresponding features of the illustrated device.

FIG. 1 shows a single unbranched glass optical fiber 2, to which is attached at the end 4 thereof, in one embodiment, by fusion, substantially non-porous (but convertible to porous) glass tip 6. In another embodiment, 2 is a single unbranched glass optical fiber fabricated from substantially non-porous glass convertible to porous glass, which at the end denoted 4 may potentially be treated as described herein to render the tip porous, e.g. in region denoted 6, up to the broken line. In FIG. 2, tip 6 of the device of FIG. 1 (either embodiment) has been made porous in the manner described herein, and thus now incorporates pores such as those denoted by reference numeral 8. Following adsorption of active substance on the inner surfaces of pores 8, tip 6 as well as at least part of the adjacent portion 4 of glass optical fiber 2 may optionally be coated with porous polymeric film 10.

In FIG. 3, two glass optical fibers 12 and 14 are fused together in the vicinity of one end, at region 16; in one embodiment, this end of the fused-together pair of fibers is attached by fusion in region 18' to a single substantially non-porous glass tip 18, whereas in another embodiment, when the fibers are fabricated from substantially non-porous glass convertible to porous glass, the structure already contains a non-porous tip 18, convertible to a porous tip. In FIG. 4, tip 18 of the device of FIG. 3 (either embodiment) has been made porous in the manner described herein, and thus now incorporates pores such as those denoted by reference numeral 8. Following adsorption of active substance on the inner surfaces of pores 8, tip 18, and at least part of the adjacent portion 18', of the glass optical fiber, may optionally be coated with porous polymeric film 20.

Figure 5:
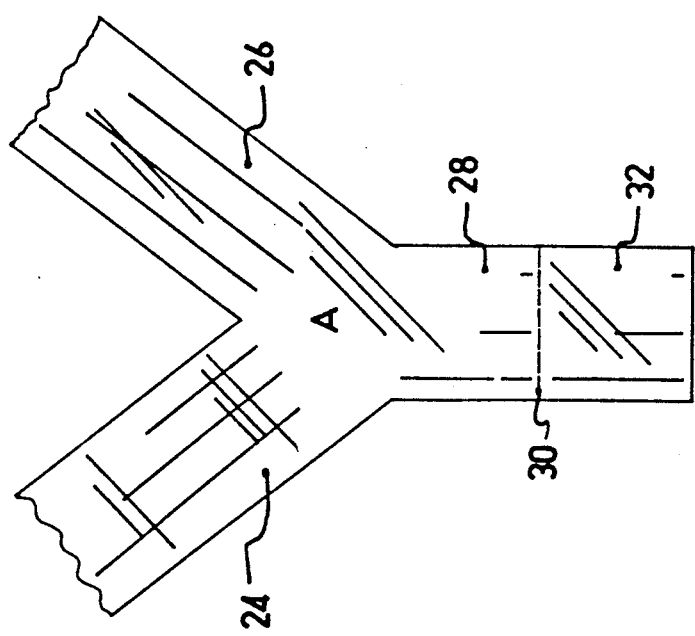
FIG. 5 shows in section a sensing device according to an embodiment of the invention which comprises a Y-shaped glass optical fiber.

In FIG. 5, a glass fiber continuum including Y-shaped junction A from which extends respective arms 24 and 26, is, in one embodiment, attached at end 28 to a substantially non-porous glass tip 32 at fusion region 30; in another embodiment, in which the glass fiber continuum is fabricated from substantially non-porous glass convertible to porous glass, 32 represents a region (bounded e.g. by broken line 30) which may potentially be made porous. In FIG. 6, tip 32 of the device of FIG. 5 (either embodiment) has been made porous in the manner described herein, and thus now incorporates pores such as those denoted by reference numeral 8. Following adsorption of active substance on the inner surfaces of pores 8, tip 32 as well as part of the adjacent portion 28 (inclusive of region 30) of the glass optical fiber may optionally be coated with porous polymeric film 34. As a variation of the embodiments of FIGS. 5 and 6, arm 28 may be replaced by a plurality of separate arms attached (e.g. by fusion) to the apex of the V formed by arms 24 and 26; these separate arms, with respective sensitized tips which are as described either attached thereto or integral therewith, may be used as separate sensors, or as a bundle as described below with reference to FIG. 8.

In the embodiments illustrated in FIG. 2, both the light directed to the sensitized tip 6 and that emitted therefrom will be channelled along the same optical fiber 2. In the embodiments illustrated in FIG. 4, it is intended that the light directed to sensitized tip 6 will be channelled along one of optical fibers 12 and 14, and that the emitted light will be mainly channelled along the other of these optical fibers. In the embodiments illustrated in FIG. 6, it is intended that the light directed to the sensor will be channelled along one arm (24 or 26) of the Y to the junction A and thereafter to the sensitized tip 32, and that the emitted light will be channelled therefrom to junction A and thereafter (mainly) along the other of arms 24 and 26.

FIG. 7 depicts the adsorption of active substance at a number of sites 22 on the inner surface of a typical pore 8.

FIG. 8 shows a bundle of individual glass optical fibers 40, 42, 44 and 46. According to one embodiment, to the respective ends of these fibers there are attached by fusion in respective regions 60, 62, 64 and 66, individual tips 50, 52, 54 and 56; according to another embodiment in which the fibers are fabricated from substantially non-porous glass convertible to porous glass, regions 50, 52, 54 and 56, bounded respectively by (e.g.) lines 60, 62, 64 and 66, may be made porous and thereafter sensitized as described herein. The bundle of fibers may in either embodiment be held together by insertion in a flexible sleeve (not shown). In the first mentioned embodiment, the fusion is effected individually with non-porous glass tips convertible to porous glass tips, and the steps of making the tips porous, adsorption of sensitive material and (if desired) coating with a porous polymeric material, are effected as described herein. The optional coating step may of course also be carried out in the case of the second mentioned embodiment. It will be appreciated that in this bundle of fibers, each tip which has been made porous may be sensitized by adsorption of a different substance, thereby making possible the simultaneous analysis of different properties of the medium in which the sensor is inserted. While a bundle of four sensors is shown in FIG. 8, alternatively a bundle of two, three or of more than four sensors, may of course also be utilized.

The invention will now be illustrated by the following non-limiting examples.

EXAMPLE 1

Preparation of parent glass and optical fibers having porous glass tips (i) Milled sand (674 g.), boric acid (457 g.) and sodium carbonate (119 g.) were melted in a 1 l. alumina crucible at 1500°–1520° C. in a gas furnace for 1.5 hours. The glass (approximately 1 kg.) was cast, broken into pieces and remelted at 1520° C. in an electrical furnace for 2 hours. It was then cast into a steel mold, pressed into a plate about 15 mm. thick and placed in a furnace at 400° C. for annealing. This plate was cut to rods ~15×15×40 mm. The resultant parent glass had the composition (wt. %):

$SiO_2 67.4; B_2O_3 25.7; Na_2O 6.9$.

(ii) Graded index 100–140 plastic coated glass optical fibers made by Israel Product Research Co. Ltd., Herzlia, Israel were used in 2.5 m. lengths. Approximately 10 cm. length of the plastic coating was removed at one end of each fiber, using 1,2-dichloroethane; the exposed parts were cleaned well in an ultrasonic bath using successively 1,2-dichloroethane (followed by shaking off excess solvent and air drying), water and ethanol, and finally hot air drying to obtain a product at this stage which was free of grease and moisture.

The parent glass from part (i) (approx. 50 g.) was remelted at 950° C. in an electrical furnace. At this temperature the glass was sufficiently fluid to draw fibers. The end of a parent glass fiber was fused in a flame to the end of a commercial glass optical fiber (prepared as described in the preceding paragraph), removing almost all the parent glass, leaving only a small fused glass tip. Alternatively, the ends of commercial glass optical fibers were dipped into molten parent glass, and the fibers were then pulled out with their tips coated with parent glass. In the product, the parent glass tip had a diameter in the range 100–500 μm.

(iii) The parent glass tip of the product of part (ii) (produced by either alternative) was heated in an electrical furnace for 25 hours at 610° C., then for 75 hours at 530° C., the heating rate being 3°–5° C. per minute. The heat-treated tip was then subjected to concentrated aqueous sodium hydroxide for 0.5 hour to remove the surface layer, and leached with 3N aqueous HCl for 25 hours at ~50° C. The specific area of the resultant porous glass tip was 120–140 $m^2/g$.

EXAMPLE 2

Adsorption of light-sensitive material on porous glass tips

A porous glass tip prepared as above and reactivated by heating gradually to 100° C. for 2 hours, was treated for 1 hour with a $10^{-4}M$ chloroform solution of perylene-3,9,-dicarboxylic acid diisobutyl ester, known commercially as "Fluorogelb". (In general, the duration of adsorption may be up to say 45 hours, and a more dilute solution e.g. $10^{-5}M$ may be used. A higher concentration such as $10^{-3}M$ causes decay of the fluorescence, while a lower concentration of the order of $10^{-6}M$ does not afford sufficient sensitivity.) Unadsorbed solution was drained off. The tip was air-dried, washed in a physiological serum, then vacuum-dried for 1 hour at 45° C. [The required serum was prepared by dissolving in 1000 ml. of double distilled water NaCl (8 g.), KCl (0.2 g.), disodium hydrogen phosphate (1.15 g.) and potassium dihydrogen phosphate (0.2 g.).] The product was stable, and no evidence of bleeding of the fluorescent material therefrom has been observed. It may be kept in the dry or wet state. The wavelengths of excitation and emission of the sensor thus prepared were 468 and about 515 nm, respectively. In the presence of oxygen, the intensity of the signal emitted from the sensor decreased by a factor of about 4 (as measured by a fluorescence counter) by comparison with pure nitrogen. Porous glass tips fused to glass optical fibers and having a different light-sensitive material adsorbed thereon, e.g. pyrene, can be prepared similarly. In the case of pyrene, the relevant wavelengths are: excitation 345 and 350 nm, emission 398 nm.

EXAMPLE 3

Coating the sensors with a porous polymeric film

A solution of 1 g. RTV silicone marketed under the trade name "Dow Corning Silastic 890 (or 891)" in 150 ml. toluene was prepared. The product of the preceding example was dipped therein and curing was effected at room temperature over a 48 hour period. The porous polymeric film extended over the sensitized porous tip and about 10 cm. along the adjacent fiber. The device was now ready for determination of the partial pressure of oxygen.

EXAMPLE 4

Correlation of light emission with oxygen content of a test gas

The product of Example 3 was set up with the sensitized tip in a chamber and in such manner that incident light was led through the fiber to the sensor and emitted light was conducted through the fiber from the sensor to a photomultiplier and means for recording the intensity of the emitted light. 100% nitrogen was led through the chamber at a rate of about 300 c.c./min. and the intensity of the light emitted from the sensor was noted. At approximately 10 second intervals, the composition of the feed gas was changed so as to increase its oxygen content initially from 0 to about 6.67% by volume and thereafter in steps of about 6.67% by volume, so that after 2.5 minutes the gas contained 100% oxygen. The intensity of the light emitted from the sensor was noted at each step of increasing the oxygen content. It was found that over the greater part of the composition range there was a substantially linear correlation between the amount of reduction of the intensity of the emitted light, corresponding with an increase in the oxygen content of the feed gas. A similar result is obtained when the sensor is immersed in an aqueous medium, through which the feed gas is bubbled.

EXAMPLE 5

Preparation of parent glass optical fibers and such fibers having integral porous glass tips (i) Parent glass (approx. 50 g.) prepared according to the details given in Example 1 part (i) was remelted at 950° C. in an electrical furnace. At this temperature the glass was sufficiently fluid to draw fibers.

(ii) A selection was made from fibers formed according to part (i), for use as optical fibers. The tips were heat-treated in an electrical furnace for 25 hours at 610° C., then for 75 hours at 530° C., the heating rate being 3°–5° C. per minute. After cooling, the tips of the optical fibers were immersed in 3N aqueous HCl for 25 hours at ~50° C. The specific area of the resultant porous tips of the glass fibers was 120–140 m²/g.

The integral porous tips of the product were reactivated and impregnated with "Fluorogelb" according to the details given in Example 2, above, with similar results. The resulting sensors were coated with a porous polymeric film as described in Example 3. Correlation of light emission with oxygen content of a test gas was carried out as detailed in Example 4, with similar results.

While embodiments of the invention have been particularly described, it will be appreciated by those skilled in the art that many variations and modifications are possible. For example, although the utilization of glass optical fibers has been described above, it will be evident that other compatible inorganic optical fibers may be substituted for these glass optical fibers at least in the embodiment of the invention wherein the glass optical fibers are fused to glass tips which (as described herein) may be converted to porous tips which are subsequently impregnated with light sensitive materials and that the obtained sensors employing such other compatible inorganic optical fibers may be regarded as the chemical and/or mechanical equivalents of those which are particularly described herein. Examples of such are the fused silica optical fibers obtainable from such suppliers as Fiberguide Industries, Polymicro Technologies and Ensign-Bickford Optics Company (U.S.A.). Preliminary experiments by the present inventors have shown that the substitution of such fused silica optical fibers for the glass optical fibers give products which appear to give less background noise and therefore possess potentially even more sensitivity than the glass fiber products. The invention is therefore not to be construed as limited by the embodiments particularly described herein, but the principles thereof may be practised within the spirit of the invention as will be apparent to those skilled in the art.

We claim:

1. A sensing device for quantitative determination of the chemical properties of a medium in situ, said device comprising at least one glass optical fiber means having a porous fused glass tip, said fused glass tip being treated after fusing with heat, alkali and acid to render it porous internally.

2. Device according to claim 1, wherein said porous glass tip has on the internal surface of the pores thereof at least one substance selected from the group consisting of fluorescent and other light sensitive substances.

3. Device according to claim 2, wherein said at least one substance is an agent which imparts information exclusively by means of internally unmodified intensity of light emitted therefrom.

4. Device according to claim 1, wherein said at least one glass optical fiber means comprises a single glass optical fiber means.

5. Device according to claim 1, wherein said at least one glass optical fiber means comprises a plurality of glass optical fiber means each of which has attached thereto a different porous glass tip.

6. Device according to claim 5, wherein each respective porous glass tip has on the internal surface of the pores thereof a substance selected from the group consisting of fluorescent and other light sensitive substances, such that at least two porous glass tips have adsorbed different said substances, respectively, whereby the device is adapted for the determination of at least two different chemical properties of said medium.

7. Device according to any one of claim 6, wherein each porous glass tip is coated with a porous polymeric film.

8. A sensing device according to claim 1 wherein said fused glass tip includes at least one substance from the group consisting of fluorescent and other light-sensitive substances.

9. Device according to claim 8, wherein said at least one substance is at least one fluorescent substance which is sensitive to ultraviolet light.

10. A sensing device according to claim 1 wherein said glass optical fiber means comprises fused silica.

11. Apparatus for quantitative determination of the chemical properties of a medium in situ, which comprises as an optic probe a sensing device which comprises at least one glass optical fiber means including an internally porous glass tip which has been obtained by converting a substantially non-porous glass tip fused thereto and which has on the internal surface of the pores thereof at least one substance selected from the group consisting of fluorescent and other light sensitive substances.

12. Apparatus according to claim 11, wherein said at least one substance is at least one fluorescent substance which is sensitive to ultraviolet light.

13. Apparatus according to claim 11, wherein said at least one substance is an agent which imparts information exclusively by means of internally unmodified intensity of light emitted therefrom.

14. Apparatus according to claim 11, wherein said at least one glass optical fiber means comprises a single glass optical fiber means.

15. Apparatus according to claim 11, wherein said at least one glass optical fiber means comprises a plurality of glass optical fiber means each of which has fused thereto a porous glass tip.

16. Apparatus according to claim 15, wherein at least two porous glass tips have on the internal surface of the pores thereof different said substances, respectively, whereby the device is adapted for the determination of at least two different chemical properties of said medium.

17. Apparatus according to claim 11, wherein the or each porous glass tip is coated with a porous polymeric film.

18. Apparatus according to claim 17, wherein said film extends to a portion of the glass optical fiber means adjacent to the or each porous tip.

19. Apparatus for quantitative determination of the chemical properties of a medium in situ, which comprises as an optic probe a sensing device which comprises at least one fused silica optical fiber means including an internally porous glass tip which has been obtained by converting an internally substantially non-porous glass tip fused thereto and which has on the internal surface of the pores thereof at least one substance selected from the group consisting of fluorescent and other light sensitive substances.

* * * * *